United States Patent [19]

Brossi

[11] Patent Number: 4,552,962
[45] Date of Patent: * Nov. 12, 1985

[54] ANTITUSSIVE 6-KETO MORPHINANS OF THE (+)-SERIES

[75] Inventor: Arnold Brossi, Bethesda, Md.

[73] Assignee: The United States of America as represented by the Department of Health and Human Services, Washington, D.C.

[*] Notice: The portion of the term of this patent subsequent to Jun. 14, 2000 has been disclaimed.

[21] Appl. No.: 459,796

[22] Filed: Jan. 21, 1983

[51] Int. Cl.$^4$ .......................................... C07D 221/28
[52] U.S. Cl. .................................................. 546/74
[58] Field of Search ........................... 546/74; 424/260

[56] References Cited

U.S. PATENT DOCUMENTS

| 2,744,112 | 5/1956 | Vogler | 546/74 |
| 3,166,559 | 1/1965 | Sawa et al. | 546/74 |
| 3,914,232 | 10/1975 | Mohacsi et al. | 546/74 |
| 3,914,233 | 10/1975 | Mohacsi et al. | 546/74 |
| 4,362,870 | 12/1982 | Portoghese | 546/44 |
| 4,388,463 | 6/1983 | Brossi et al. | 546/74 |
| 4,390,699 | 6/1983 | Brossi et al. | 546/74 |
| 4,410,700 | 10/1983 | Rice | 546/44 |

OTHER PUBLICATIONS

Hellerbach, et al., "Synthetic Analgesics", part IIa, Pergamon Press, pp. 96-103 (1966).
Brossi, et al., J. Org. Chem., vol. 47(26), pp. 5214-5216 (1982).
Schmidhammer, et al., Can. J. Chem., vol. 60, pp. 3055-3060 (1982).
Hsu, et al., Helv. Chim. Acta., vol. 63(7), pp. 2042-2045 (1980).
Hsu, et al., Helv. Chim. Acta., vol. 65, pp. 1576-1589 (1982).
Manmade, et al., Chemical Abstracts, vol. 96, 181468j (1982).
Brossi, et al., Helv. Chim. Acta., vol. 64(5), pp. 1672-1681 (1981).
Jacobson, et al., Helv. Chim. Acta., vol. 64(5), pp. 1298-1302 (1981).

Primary Examiner—Donald G. Daus
Assistant Examiner—W. A. Teoli, Jr.
Attorney, Agent, or Firm—John S. Roberts, Jr.

[57] ABSTRACT

The present invention is concerned with dextrorotatory morphinans, which are illustrated by (+)-4-methoxy-6-keto-N-methylmorphinan. Related compounds which also have been introduced as cough-suppressing agents include the (+)-3-methoxy-N-methylmorphinans (ROMILAR-Roche).

6 Claims, No Drawings

ANTITUSSIVE 6-KETO MORPHINANS OF THE (+)-SERIES

The present invention is concerned with dextrorotatory morphinans, which are illustrated by (+)-4-methoxy-6-keto-N-methylmorphinan. Related compounds which also have been introduced as cough-suppressing agents include the (+)-3-methoxy-N-methylmorphinans (ROMILAR-Roche).

PRIOR ART STATEMENT

Brossi, et al, *J. Org. Chem.*, Vol. 47, 5214–4216 (1982).

Schmidhammer and Brossi, "Synthesis of (−)- and (+)-2-Hydroxy-6-keto-N-methylmorphinans, Their O-Methyl Ethers and 2-Deoxy-Cogeners," *Can. J. Chem.*, 60:3055 (1982).

Hsu, et al, *Helvetica Chimica Acta*, Vol. 65, pp. 1576–1589 (1982).

Hellerbach et al, Synthetic Analgesics, Vol. 8, Parts IIA, IIB, Pergamon Press, 1966, pp. 96–103.

U.S. Pat. No. 3,810,899, Mohacsi.
U.S. Pat. No. 3,914,232, Mohacsi.
U.S. Pat. No. 3,914,233, Mohacsi.

THE INVENTION

A classical example of discrimination of biological activity through optical isomers was the finding that the (−)-morphinans of the natural series of opioids bind to the opiate receptor and exhibit analgetic activity, whereas their (+)-isomers do not bind to the opiate receptor, have no analgetic effects but are antitussive agents (see Hellerbach et al, ante). This discovery led to the finding and marketing of dextromethorphan by Roche (dextromethorphan=(+)-3-methoxy-N-methylmorphinan). It has now been found that (+)-6-ketomorphinans, belonging to the unnatural series of morphinans and obtained by total synthesis, have even better antitussive properties in experimental animals, and seem to be longer acting and more potent than dextromethorphan or codein.

The preparation and production entailing these antitussive compounds are the content of this application.

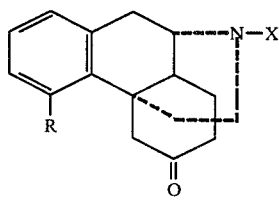

R=H, OH, OMe
x=H, Me

This invention covers the compounds listed above, belonging to the unnatural (+)-series of ketomorphinans, showing useful antitussive activity in form of their free bases or appropriate salts, such as hydrobromides, phosphates, succinates, salicylates, sulfates, hydrochlorides, nitrates, tartrates, etc. by standard pharmacological tests.

Preparation

Scheme I

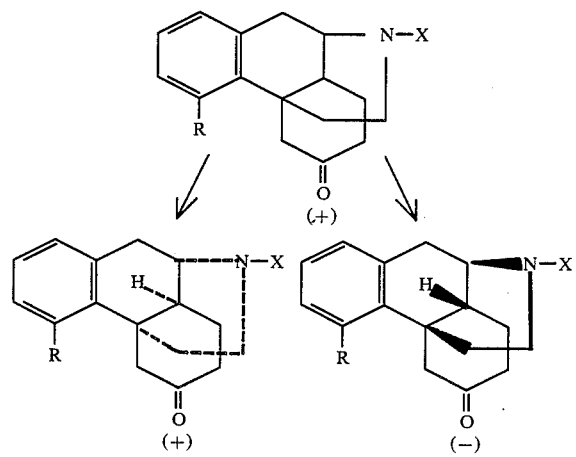

Racemic ketomorphinans of the above formula (R=H or OMe) have been prepared (R=H, Schmidhammer et al, *Can. J. Chem.*, in press; R=OMe, Brossi et al, *J. Org. Chem.*, 47:5214, 1982). These compounds containing equal amounts of (−)- and (+)-isomers are called racemic mixtures, or racemates, and can be resolved by chemical resolving agents, such as d- and l-tartaric acids or their derivatives, d- and l-camphorsulfonic acids, d- and l-malic acids, etc. Separation of racemic materials of the above structure is usually carried out by dissolving the base in a solvent such as alcohols, acetone, water, etc. After adding an appropriate amount of the resolving agent, one of the two optical isomers (a or b), crystallizes out in the form of a salt and the other can be recovered from the mother liquor. The sign of optical rotation of the free base can easily be detected from the sign of the optical rotation measured and, if found to be (−), the compound belongs to the natural series of ketomorphinans. This application only covers the ketomorphinans showing a (+)-rotation and belonging to the unnatural series of ketomorphinans.

For example, (±)-4-methoxy-N-methylmorphinan of m.p. 111°–112° was prepared by total synthesis (see Brossi et al, *J. Org. Chem.*, 47:5214–5216, Dec. 17, 1982), when dissolved in methanol and added with a stechiometric amount of (−)-dibenzoyl-L-tartaric acid in methanol. After standing over night, the salt was separated, crystallized twice from methanol and then converted into its free base by treatment with an aqueous solution of sodium hydroxide and methylenechloride. The crystalline base obtained after evaporation and crystallization from benzene/petroleum ether had m.p. 145°–147° and $[\alpha]_D = 96.5°$ (CHCl$_3$). From the mother liquor the (+)-isomer could be obtained after isolation of the free base, preparation of the dibenzoyl-tartrate salt with (+)-dibenzoyl-D-tartaric acid, crystallization and conversion into the free base, having the same melting point but an opposite rotation.

Compounds including the free bases and pharmaceutically acceptable acid addition salts representative of this invention are (+)-N-methylmorphinan-6-one
(+)-Morphinan-6-one
(+)-4-Methoxy-morphinan-6-one (+)-4-Methoxy-N-methylmorphinan-6-one
(+)-4-Hydroxy-morphinan-6-one
(+)-4-Hydroxy-N-methylmorphinan-6-one Further, an example to convert 4-methoxymorphinan-6-ones into 4-hydroxymorphinan-6-ones with HBr is given in the paper by Brossi et al, *J. Org. Chem.* 47:5214–16 (1982).

d-tartaric acid in methanol, following procedures given by Schmidhammer et al in the 2-hydroxy series (*Can. J. Chem.*, 1982, 60:3055).

For the conversion of 1 into the desired ketomorphinans of the unnatural series, the base was reduced with an alkali metal in liquid ammonia in the presence of t-BuOH (Hsu et al, *Helv. Chim. Acta*, 65:1576, 1982) to afford 2, and after N-protection with ethylformate, the

SCHEME II

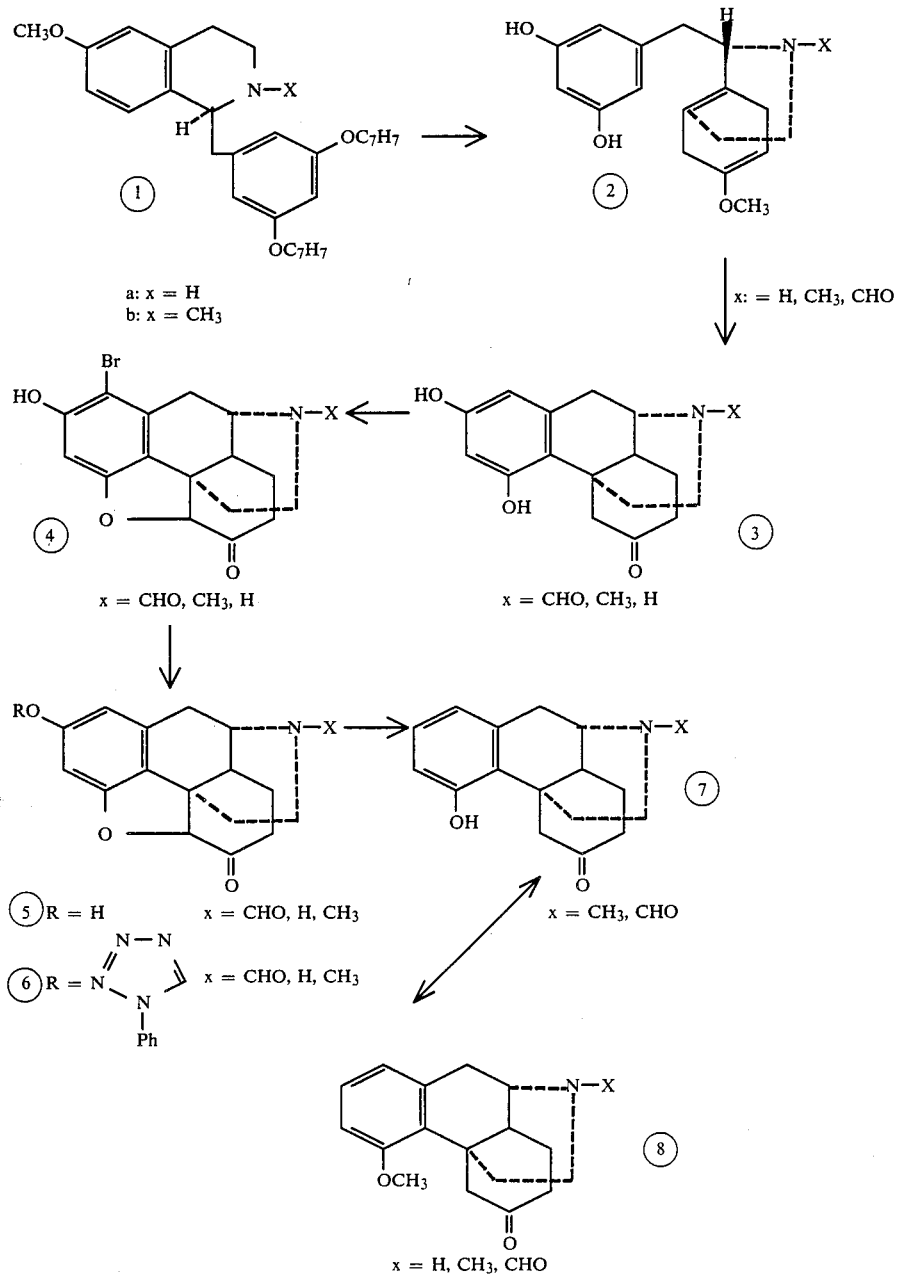

In the synthesis of the 4-methoxy-substituted 6-ketomorphinans 8 (Scheme II above) of the unnatural (+)-series of ketomorphinans, the chemistry took a similar course as that described in the (±)-series by Hsu et al (*Helv. Chim. Acta*, 65:1576, 1982) and in the (−)-series as described by Rozwadowska et al, *Can. J. Chem.*, 58:1855 (1980). In the present invention, the oily base 1 was obtained by optical resolution of (±)-1 with N-formyl derivative 2. If TIQ 1 is first N-methylated with formaldehyde in the presence of sodium-cyanoborohydride, 1 was obtained, and after Birch reduction, 2. Cyclization of 2 with mineral acids such as HCl, H₂SO₄, etc., affords the desired 6-ketomorphinans 3 of the (+)-series. The elimination of the 2-OH group in 3 was accomplished after cyclization with bromine, followed by dehydrobromination with base, such as aqueous NaOH (see Hsu above). This afforded the ketones of formula 4, brominated at C-1. The bromine could be removed by catalytic hydrogenation over Pd/C in acetic acid in the presence of acetate to afford 5. Reaction of the phenols 5 with N-phenylchlorotetrazol (see Hsu above) afforded the ethers 6 and after catalytic reduction over Pd/C in acetic acid at 40°–60° directly the ketones 7 of the (+)-series. The conversion of 5 into 7 was accomplished by first removing the oxygen function at 2-OH by catalytic reduction of its N-phenyltetrazolyl ether, followed by opening of the oxide-bridge with metallic Zn in boiling methanol in the presence of ammonium chloride (see Rozwadowska, ante). O-methylation of 7 with phenyltrimethylammoniumchloride (see Hsu, ante) afforded directly 8. The antitussive 8 was also obtained from 7 after O-methylation (see Rozwadowska, ante, and Hsu, Rice and Brossi, *Helv. Chim. Acta*, 65:1576–1589, 1982), removal of the N-protecting group by acid hydrolysis and reductive N-methylation of the intermediate 8. Compound 8 is the unnatural optical isomer of the opioid prepared from natural morphine and showed as expected identity and the opposite optical properties.

UTILITY

When tested as antitussive agents and compared with codeine and dextromethorphane as standards in lightly anesthetized cats with cough reflexes elicited by mechanical stimulation of the tracheal mucosa, compounds 8 showed excellent activity as selected members of the present compounds.

6-Ketomorphinans of the (+)-Series with Antitussive Activity

This invention reports the preparation of (+)-6-ketomorphinans of formula 1, which show exceptional antitussive activity and are of therapeutic value. They cannot be prepared from natural opioids, which have an enantiomeric configuration and, since unnatural opioids are scarce, have to be prepared by total synthesis. This invention covers the compounds shown in formula 1, where R is H, OH, OMe and where the N-substituent is either H or Me, or a pharmacological equivalent, such as n-propyl, phenethyl, etc.

It has long been known that morphinans of the unnatural (+)-series of opioids, being optical antipodes of naturally derived morphinans, do not bind to the opiate receptor, do not have narcotic analgetic activity but exhibit profound antitussive effects. It was shown that dextromethorphane, developed based on this knowledge, has useful therapeutic properties as a nonnarcotic antitussive agent. Although chemical manipulation of dextromethorphan has afforded similarly active compounds, none was found to be superior to dextromethorphan with regard to potency and/or duration of action. The compounds, designated by structure 1, showed equal or superior antitussive activity, and therefore have properties to mark them as novel and superior antitussive agents. The compounds have been prepared by total synthesis, including as a major step the separation into optical isomers. Such a separation can be accomplished with racemic compounds obtained by total synthesis at the stage of the morphinan structure, affording equal parts of natural compounds called (−)-isomers and unnatural compounds, called (+)-isomers. This separation can be accomplished very early in the synthesis or at the morphinan stage. In the latter case, equal amounts of unwanted (−)-isomers are obtained in addition to the wanted (+)-isomers. Since this procedure is not economical, a separation into optical isomers was preferably done at an earlier stage.

A further preparation of the compounds of the present invention is illustrated below for the 2-hydroxy-6-keto compounds, which is a similar process parallelling the steps for the present process and the 4-hydroxy compounds, and will afford analogous products such as a 12 product (Scheme III) in the present invention. If the racemate is secured at 4, then the unnatural series of (+) compounds lead to the desired series of (+) compounds as in 12.

SCHEME III

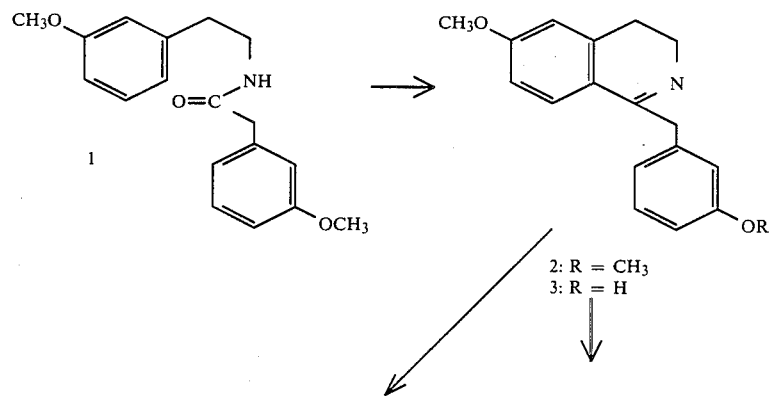

2: R = CH₃
3: R = H

SCHEME III

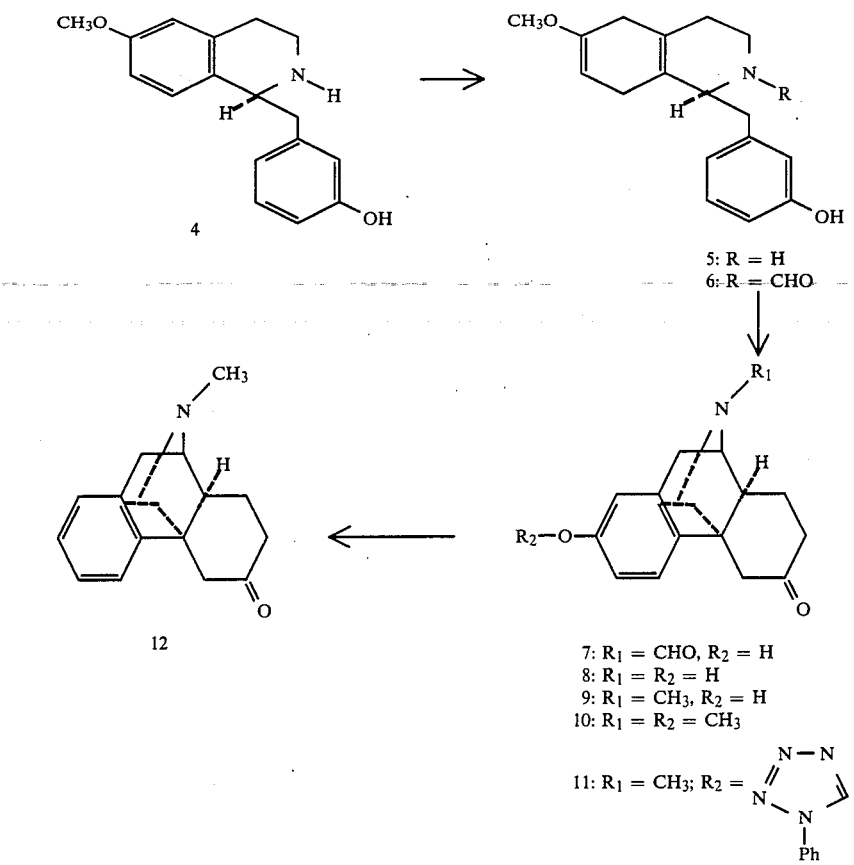

7: $R_1$ = CHO, $R_2$ = H
8: $R_1$ = $R_2$ = H
9: $R_1$ = $CH_3$, $R_2$ = H
10: $R_1$ = $R_2$ = $CH_3$

11: $R_1$ = $CH_3$; $R_2$ = 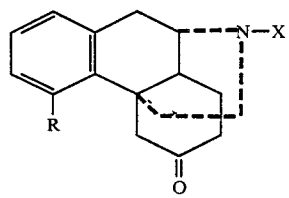

The 4-OH and 4-OMe compounds, shown in Scheme II, were prepared according to the following examples. These examples, from Brossi et al, *J. Org. Chem.*, 47:5214-16 (1982), show the preparation of (+)-4-methoxy compound 8 in Scheme II from the conversion of the 4-methoxy-N-methylmorphinan-6-one to 4-hydroxy-N-methylmorphinan-6-one.

EXAMPLE 1

(+)-4-Methoxy-N-methylmorphinan-6-one

4-Methoxy-N-methylmorphinan-6-one (8, X=$CH_3$) was prepared from 4-hydroxy-N-methylmorphinan-6-one (7, X=$CH_3$) as shown in the racemic series (*J. Org. Chem.*, 47:5214, 1982). The product was recrystallized from benzene/petroleum ether: mp 145°-147° C.

EXAMPLE 2

(+)-4-Hydroxy-N-methylmorphinan-6-one

To a solution of 8 (Scheme II, X=$CH_3$) (100 mg, 0.35 mmol) in 6 mL of $CHCl_3$ was added $BBr_3$ (3 g, 12.0 mmol) at −70° C. The mixture was stirred at −70° C. for 2 h, poured into ice/$H_2O$, and washed with ether. The aqueous solution was rendered alkaline to pH 8 with concentrated aqueous $NH_3$ and extracted with $CHCl_3$. The $CHCl_3$ layer was washed with brine, dried ($Na_2SO_4$), and evaporated to afford a yellow residue. Column chromatography (alumina, $CHCl_3$, then $CHCl_3/CH_3OH$=50:1) of the crude material gave 4-hydroxy-N-methylmorphinan-6-one (7, Scheme II, X=$CH_3$)(65 mg, 68%): mp $HBr.SO_4$ 210° C.

I claim:

1. The unnatural isomer free from its optical antipode

R=H, OMe
x=H, Me and pharmaceutically acceptable acid addition salts.

2. (+)-N-Methylmorphinan-6-one free from its optical antipode.

3. (+)-Morphinan-6-one free from its optical antipode.

4. (+)-4-Hydroxymorphinan-6-one free from its optical antipode.

5. (+)-4-Methoxy-morphinan-6-one free from its optical antipode.

6. (+)-4-Methoxy-N-methylmorphinan-6-one free from its optical antipode.

* * * * *